(12) United States Patent
Makino

(10) Patent No.: US 11,010,895 B2
(45) Date of Patent: May 18, 2021

(54) PROCESSOR FOR ELECTRONIC ENDOSCOPE AND ELECTRONIC ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 16/642,595

(22) PCT Filed: Oct. 24, 2018

(86) PCT No.: PCT/JP2018/039496
§ 371 (c)(1),
(2) Date: Feb. 27, 2020

(87) PCT Pub. No.: WO2019/087895
PCT Pub. Date: May 9, 2019

(65) Prior Publication Data
US 2020/0258217 A1   Aug. 13, 2020

(30) Foreign Application Priority Data

Nov. 2, 2017 (JP) .............................. JP2017-212872

(51) Int. Cl.
*G06T 7/00* (2017.01)
*H04N 7/18* (2006.01)

(52) U.S. Cl.
CPC ............ *G06T 7/0012* (2013.01); *H04N 7/183* (2013.01)

(58) Field of Classification Search
None
See application file for complete search history.

(56) References Cited

U.S. PATENT DOCUMENTS

2002/0196335 A1 * 6/2002 Ozawa ................. H04N 9/735
2003/0076412 A1   4/2003 Ozawa
(Continued)

FOREIGN PATENT DOCUMENTS

JP   2003-010113   1/2003
JP   3869698      1/2007
(Continued)

OTHER PUBLICATIONS

International Search Report issued in International Patent Application No. PCT/JP2018/039496, dated Jan. 15, 2019.

*Primary Examiner* — Edemio Navas, Jr.
(74) *Attorney, Agent, or Firm* — Greenblum & Bernstein, P.L.C.

(57) ABSTRACT

A processor for an electronic endoscope includes an enhancement processing unit that includes: a depth data generation unit configured to generate depth data D of the entire captured image by generating, a data value representing information on a depth of a concave portion of the living tissue in each pixel; an undulation-enhanced data generation unit configured to generate a value of undulation-enhanced data S, which has information with a steeply inclined change of a signal level value at a boundary between a concave portion and a convex portion of surface irregularities of the living tissue, from the depth data D; and an enhancement processing execution unit that generates an enhanced image by adding or subtracting at least a value to or from a signal level value of the processing target pixel on which the enhancement processing of the captured image is performed.

12 Claims, 6 Drawing Sheets

(56) References Cited

U.S. PATENT DOCUMENTS

| | | | |
|---|---|---|---|
| 2015/0363942 A1* | 8/2015 | Mitsui | A61B 1/0646 |
| 2015/0257628 A1 | 9/2015 | Morita | |
| 2015/0363929 A1 | 12/2015 | Higuchi | |
| 2017/0301093 A1* | 4/2017 | Nakagomi | G06T 7/0016 |

FOREIGN PATENT DOCUMENTS

| | | | |
|---|---|---|---|
| JP | 2013-081556 | | 5/2013 |
| JP | 2013081556 A | * | 5/2013 |
| JP | 2013-153991 | | 8/2013 |
| JP | 2014-161355 | | 9/2014 |
| JP | 2014161355 A | * | 9/2014 |
| WO | 2014/103425 | | 7/2014 |
| WO | 2014/132475 | | 9/2014 |

* cited by examiner

PROCESSOR FOR ELECTRONIC ENDOSCOPE AND ELECTRONIC ENDOSCOPE SYSTEM

TECHNICAL FIELD

The present invention relates to a processor for an electronic endoscope and an electronic endoscope system that acquire a captured image of a living tissue and perform enhancement processing of the captured image.

BACKGROUND ART

An electronic endoscope device is used for observation and treatment of a living tissue inside a human body. A process of enhancing surface irregularities, which makes a concave portion visible such that the surface irregularities of the living tissue can be observed from a captured image obtained by imaging the living tissue using the electronic endoscope device, is performed on the captured image, and the resultant is displayed on a display. Since a lesion part of the living tissue has more irregularities on the surface than a healthy part, the display of the captured image with enhanced surface irregularities is useful to find the lesion part.

There is known an electronic endoscope device that can reliably highlight a concave portion on a surface of a living tissue and, as a result, can reliably diagnose even a slight lesion part without oversight (Patent Literature 1).

This electronic endoscope device generates a video color signal based on one frame of color pixel signals read from a solid-state image sensor provided at a distal tip of a scope. The electronic endoscope device includes a comparison means for comparing a signal level value of a color pixel signal corresponding to a specific pixel included in one frame of color pixel signals with signal level values of color pixel signals corresponding to all adjacent surrounding pixels adjacent to the surrounding of the specific pixel in a predetermined pixel array direction; and a color balance change means for changing color balance of a video color signal by changing the signal level value of the color pixel signal corresponding to the specific pixel according to a comparison result obtained by the comparing means.

CITATION LIST

Patent Literature

Patent Literature 1: JP 3869698 B2

SUMMARY OF INVENTION

Technical Problem

In the electronic endoscope device, a concave portion of surface irregularities of a living tissue with a mucous membrane is extracted by comparison with the signal level values of the color pixel signals corresponding to all the adjacent surrounding pixels adjacent to the surrounding of the specific pixel in the predetermined pixel array direction, and a signal level value of a specific color component of a pixel of the extracted concave portion is reduced to change a color of a portion corresponding to the concave portion, thereby creating an image with the enhanced surface irregularities.

In the above-described electronic endoscope device, the strength of the enhancement on the surface irregularities greatly depends on a difference between the signal level values of a focused pixel and the adjacent surrounding pixel. The strength of the enhancement on the surface irregularities increases as the difference between the signal level values of the focused pixel and the adjacent surrounding pixel increases. That is, the strength of the enhancement on the surface irregularities increases as the depth of the concave portion increases. Thus, it is difficult to perform sufficient enhancement in a portion where the depth of the concave portion is relatively shallow.

On the other hand, if adjustment is performed such that a shallow concave portion is enhanced more strongly than a deep concave portion, a difference in signal level value between the shallow concave portion and the deep concave portion decreases in an enhanced image, and as a result, a three-dimensional effect of surface irregularities is easily lost.

Therefore, an object of the present invention is to provide a processor for an electronic endoscope and an electronic endoscope system capable of performing enhancement processing that suppresses deterioration of a three-dimensional effect of surface irregularities of a living tissue when acquiring a captured image of the living tissue and performing the enhancement processing.

Solution to Problem

One aspect of the present invention is a processor for an electronic endoscope that acquires a captured image of a living tissue and performs enhancement processing. The processor for an electronic endoscope includes an enhancement processing unit configured to perform enhancement processing on the captured image of the living tissue. The enhancement processing unit includes: a depth data generation unit configured to generate depth data D of the entire captured image by generating a data value representing information on a depth of a concave portion of the living tissue in a focused pixel 1 based on a difference between a signal level value of the focused pixel 1 that is each pixel of the captured image and a representative value of signal level values of a plurality of adjacent pixels located around the focused pixel 1, an undulation-enhanced data generation unit configured to generate a value of undulation-enhanced data S for each pixel of the captured image, which has information with a steeply inclined change of a signal level value of the captured image at a boundary between a concave portion and a convex portion of surface irregularities of the living tissue, from the depth data D; and an enhancement processing execution unit configured to generate an enhanced image by adding or subtracting at least a value obtained by multiplying a value of the depth data D in a processing target pixel by a constant and a value obtained by multiplying the value of the undulation-enhanced data S in the processing target pixel by a constant to or from a signal level value of the processing target pixel on which the enhancement processing of the captured image is performed.

It is preferable that the undulation-enhanced data generation unit be configured to generate the undulation-enhanced data S by calculating a value obtained by attaching a plus or minus sign of the depth data D in the focused pixel 2 to a result obtained by subtracting an absolute value of a weighted average value of values of the depth data D of peripheral pixels surrounding a focused pixel 2 and a value of the depth data D of the focused pixel 2 from a weighted average value of an absolute value of the value of the depth data D in the focused pixel 2 and absolute values of the values of the depth data D of the peripheral pixels surrounding the focused pixel 2 that is each pixel of the captured image.

It is preferable that the peripheral pixels be all pixels excluding the focused pixel 2 in a range of s pixels×s pixels (s is an odd number of 3 or more) around the focused pixel 2.

It is preferable that s be an odd number in the range of 3 to 9.

It is preferable to set a pixel having a value larger than a preset value in the undulation-enhanced data S as the processing target pixel.

It is preferable that the adjacent pixels be pixels which are m-th neighboring pixels (m is a natural number of 1 or more) in at least one pixel array direction among four directions of the up-down direction, the left-right direction, the upper left-lower right direction, and the upper right-lower left direction with the focused pixel 1 as the center.

When the signal level value of the focused pixel 1 is lower than the representative value of the signal level values of the m-th neighboring pixels, it is preferable to set the focused pixel 1 as a candidate for the processing target pixel.

It is preferable that the representative value be a simple average value, a weighted average value, a median value, a minimum value, or a maximum value of the signal level values of the adjacent pixels.

It is preferable that the enhancement processing execution unit be configured to subtract a value obtained by multiplying the signal level value of the processing target pixel by a constant from the signal level value of the processing target pixel as well as adding or subtracting the value obtained by multiplying the value of the depth data D by the constant and the value obtained by multiplying the value of the undulation-enhanced data S by the constant to or from the signal level value of the processing target pixel.

It is preferable that the signal level values of the captured image include signal level values $I_k$ of color components of three colors of red, green, and blue (k is a variable to identify red, green, or blue color component and is a natural number), and that the enhancement processing execution unit generate the enhanced image using the value of the depth data D and value of the undulation-enhanced data S shared by the signal level values $I_k$ of the color components of the three colors of red, green, and blue.

It is preferable that the depth data D and the undulation-enhanced data S be data generated using a signal level value of a luminance component of the captured image, that the enhancement processing execution unit be configured to generate a signal level value $I_k^*$ of the enhanced image according to $I_k^* = I_k - \alpha_k \cdot I_k - \beta_k \cdot D - \gamma_k \cdot S$ ($\alpha_k$, $\beta_k$, and $\gamma_k$ are constants), and that $\alpha_k$, $\beta_k$, and $\gamma_k$ have different values among the color components of the three colors.

It is preferable that the above-described $\alpha_k$ and $\gamma_k$ of the red color component have larger values than the above-described $\alpha_k$ and $\gamma_k$ of at least one of the green and blue color components.

In addition, one aspect of the present invention is an electronic endoscope system that includes: the processor for an electronic endoscope; and an electronic endoscope which is connected to the processor for an electronic endoscope and outputs the captured image of the living tissue.

Advantageous Effects of Invention

According to the above-described processor for an electronic endoscope and electronic endoscope system, it is possible to perform the enhancement processing that suppresses the deterioration of the three-dimensional effect of the surface irregularities of the living tissue when acquiring the captured image of the living tissue and performing the enhancement processing.

DESCRIPTION OF EMBODIMENTS

Figure 1:
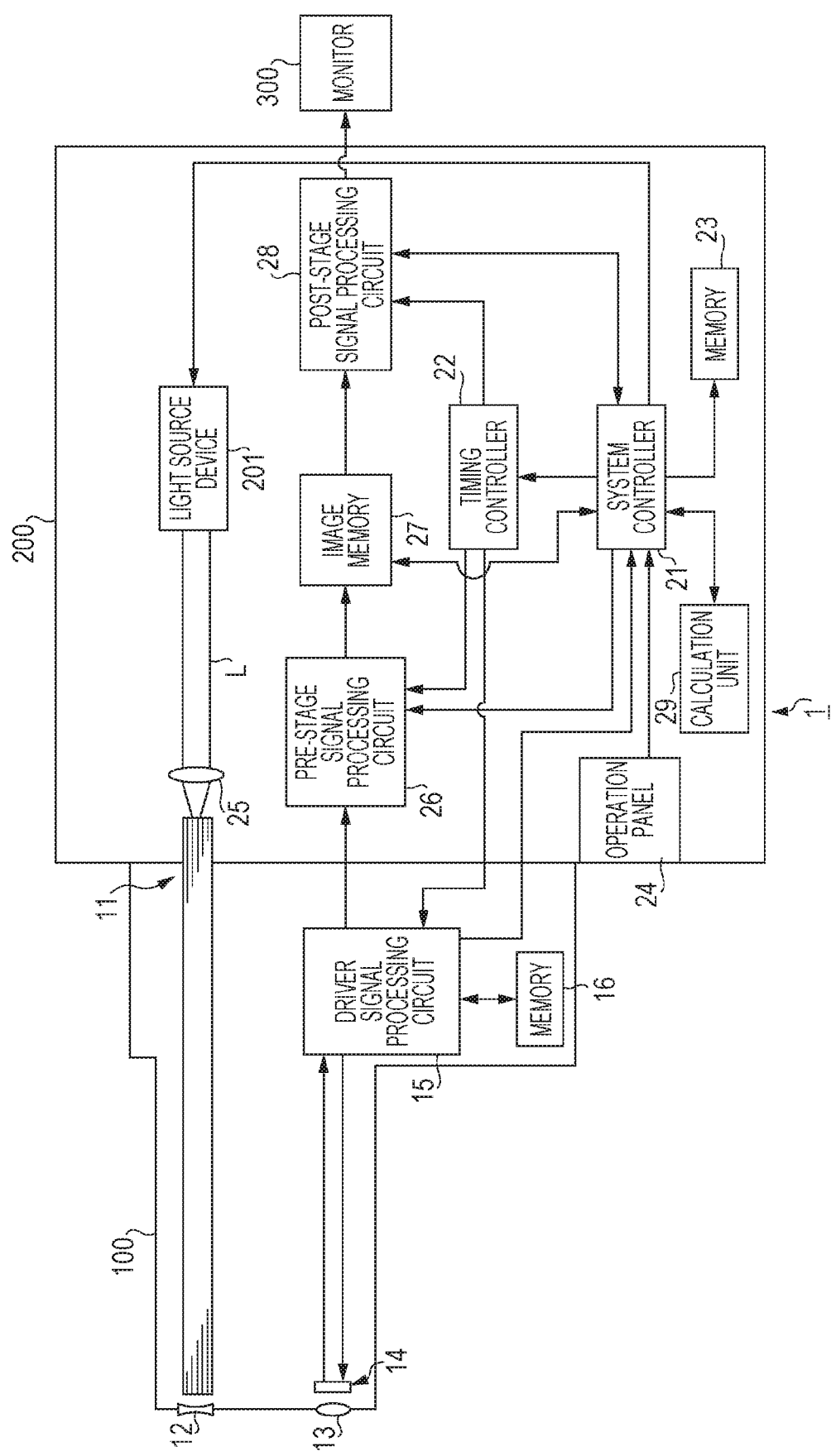
FIG. 1 is a block diagram illustrating an example of a configuration of an electronic endoscope system of the present embodiment.

A processor for an electronic endoscope according to the present embodiment extracts a region of a concave portion of a living tissue, which is a region that needs to be enhanced in a captured image obtained by imaging the living tissue, and performs the enhancement processing on this region. Examples of the region that needs to be enhanced include a plurality of concave portions having different recess depths.

The processor of the present embodiment generates an enhanced image by at least adding or subtracting a value of depth data D in a processing target pixel and a value of undulation-enhanced data S in the processing target pixel to or from a signal level value of the processing target pixel on which the enhancement processing of the captured image is performed.

Here, the depth data D is data which is created based on a difference between a signal level value of a focused pixel 1 and a representative value of signal levels of adjacent pixels located around this focused pixel 1 using each pixel of the captured image as the focused pixel 1, and represents information on a depth of a concave portion of the living tissue. The value of the undulation-enhanced data S in the processing target pixel has information with a steeply inclined change of a signal level value at a boundary between a concave portion and a convex portion of surface irregularities of the living tissue. The value of the undulation-enhanced data S in the processing target pixel is generated from the depth data D. The depth data D and the undulation-enhanced data S are generated for each pixel of the captured image.

Specifically, the processor calculates a signal level value $I^*_{ij}$ of each pixel of the enhanced image by adding or subtracting a value obtained by multiplying a value $D_{ij}$ of the depth data D of the processing target pixel by a constant and a value obtained by multiplying a value $S_{ij}$ of the undulation-enhanced data S of the processing target pixel by a constant to or from a signal level value $I_{ij}$ (i and j is information representing a pixel position, and is zero or a natural number) of the processing target pixel of the captured image.

In this manner, the processor performs the enhancement processing based on the undulation-enhanced data S including the information in which the inclination at the boundary between the concave portion and the convex portion is made steep. In this enhancement processing, a three-dimensional effect is easily lost by performing the enhancement processing with a higher degree of enhancement on a shallow concave portion in order to make the shallow concave portion stand out, but the signal level is adjusted using the undulation-enhanced data S such that a steeply inclined portion at the boundary between the concave portion and the convex portion looks even steeper, so that it is possible to suppress deterioration of the three-dimensional effect of the surface irregularities.

Hereinafter, the electronic endoscope system of the present embodiment will be described in detail with reference to the drawings.

FIG. 1 is a block diagram illustrating an example of a configuration of an electronic endoscope system 1 of the present embodiment. As illustrated in FIG. 1, the electronic endoscope system 1 is a system specialized for medical use, and includes an electronic scope (electronic endoscope) 100, a processor 200, and a monitor 300.

The processor 200 includes a system controller 21 and a timing controller 22. The system controller 21 executes various programs stored in the memory 23 and integrally controls the entire electronic endoscope system 1. The system controller 21 is connected to an operation panel 24. The system controller 21 changes each of operation of the electronic endoscope system 1 and parameters for each of the operation in accordance with an operator's instruction input to the operation panel 24. The timing controller 22 outputs a clock pulse for adjusting the operation timing of individual units to individual circuits in the electronic endoscope system 1.

The processor 200 includes a light source device 201. The light source device 201 emits illumination light L configured to illuminate an object such as a living tissue in a body cavity. The illumination light L includes white light, pseudo white light, or special light. According to one embodiment, it is preferable that the light source device 201 select one of a mode of constantly emitting white light or pseudo white light as the illumination light L and a mode of alternately emitting white light or pseudo white light and special light as the illumination light L, and emit the white light, the pseudo white light, or the special light based on the selected mode. The white light is light having a flat spectral intensity distribution in the visible light band, and the pseudo white light is light which is a mixture of light of a plurality of wavelength bands and has non-flat spectral intensity distribution. The special light is light in a narrow wavelength band, such as blue and green, in the visible light band. The light in the blue or green wavelength band is used at the time of enhancing and observing a specific portion in a living tissue. The illumination light L emitted from the light source device 201 is focused by the condenser lens 25 onto an incident end face of a Light Carrying Bundle (LCB) 11, which is a bundle of optical fibers, to be incident on the LCB 11.

The illumination light L incident on the LCB 11 propagates within the LCB 11. The illumination light L propagating through the LCB 11 is emitted from an exit end surface of the LCB 11 disposed at a distal tip of the electronic scope 100 so as to be directed to the object via a light distribution lens 12. Return light from the object illuminated with the illumination light L from the light distribution lens 12 forms an optical image on a light receiving surface of the solid-state image sensor 14 via an objective lens 13.

The solid-state image sensor 14 is a single-plate color Charge Coupled Device (CCD) image sensor having a Bayer pixel arrangement. The solid-state image sensor 14 accumulates an optical image formed by each of pixels on the light receiving surface, as charges corresponding to the amount of light, and generates and outputs image signals of Red (R), Green (G), and Blue (B). Note that the solid-state image sensor 14 is not limited to a CCD image sensor, and may be replaced with a Complementary Metal Oxide Semiconductor (CMOS) image sensor or other types of imaging devices. The solid-state image sensor 14 may include a complementary color filter.

A driver signal processing circuit 15 is provided in a connection portion where the electronic scope 100 is connected to the processor 200. An image signal of an object is input to the driver signal processing circuit 15 from the solid-state image sensor 14 at a predetermined frame cycle. The frame cycle is 1/30 seconds, for example. The driver signal processing circuit 15 performs predetermined processing on the image signal input from the solid-state image sensor 14 and outputs the processed image signal to a pre-stage signal processing circuit 26 of the processor 200.

The driver signal processing circuit 15 also accesses memory 16 and reads out device-specific information of the electronic scope 100. The device-specific information of the electronic scope 100 recorded in the memory 16 includes, for example, the number of pixels and sensitivity of the solid-state image sensor 14, an operable frame rate, a model number, or the like. The driver signal processing circuit 15 outputs the device-specific information read from the memory 16 to the system controller 21.

The system controller 21 performs various calculations based on the device-specific information of the electronic scope 100 and generates a control signal. The system controller 21 controls the operation and timing of various circuits in the processor 200 using the generated control signal so as to perform processing suitable for the electronic scope 100 connected to the processor 200.

The timing controller 22 supplies a clock pulse to the driver signal processing circuit 15 in accordance with timing control by the system controller 21. The driver signal processing circuit 15 performs driving control of the solid-state image sensor 14 at a timing synchronized with the frame rate of the video image processed on the processor 200) side in accordance with the clock pulse supplied from the timing controller 22.

The image signal is input to the pre-stage signal processing circuit 26 from the driver signal processing circuit 15 at one frame cycle.

The image signal is subjected to predetermined signal processing such as demosaic processing, a matrix operation, and Y/C separation, and is output to an image memory 27.

The image memory 27 buffers the image signal input from the pre-stage signal processing circuit 26, and further buffers an image signal of the enhanced image obtained by performing the enhancement processing on the image signal read from the image memory 27 by the calculation unit 29 again, and outputs the buffered image signal to the post-stage signal processing circuit 28 according to timing control of the timing controller 22.

The post-stage signal processing circuit 28 processes the image signal input from the image memory 27 to generate monitor display screen data, and converts the generated monitor display screen data into a predetermined video format signal. The converted video format signal is output to the monitor 300. With this processing, an image of the object is displayed on a display screen of the monitor 300.

Figure 2:
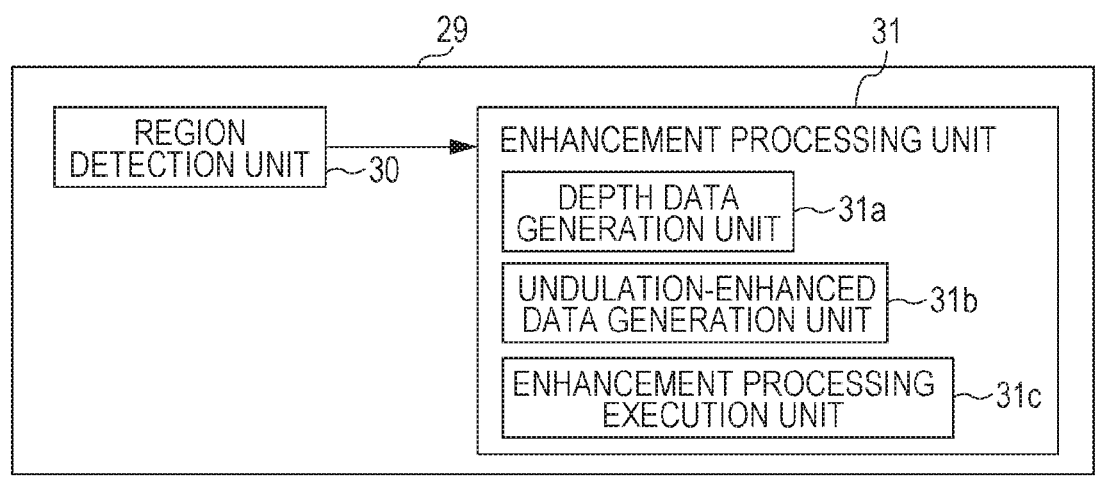
FIG. 2 is a block diagram illustrating an example of a configuration of a calculation unit illustrated in FIG. 1.
Figure 3:
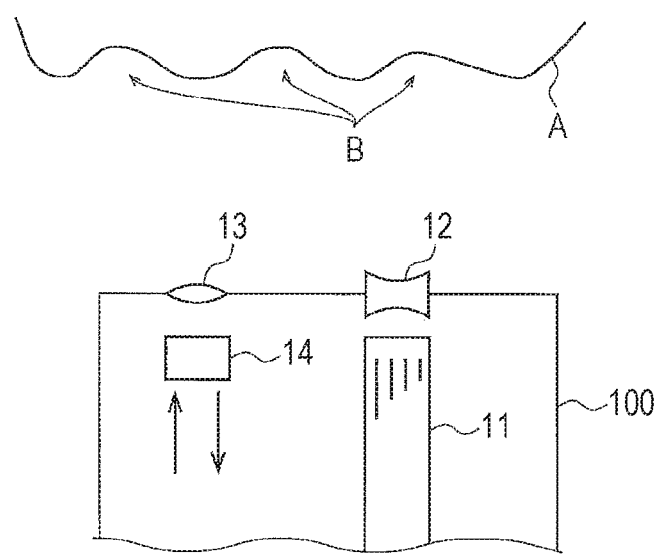
FIG. 3 is a view illustrating an example of imaging of a living tissue by an endoscope illustrated in FIG. 1.
Figure 4:
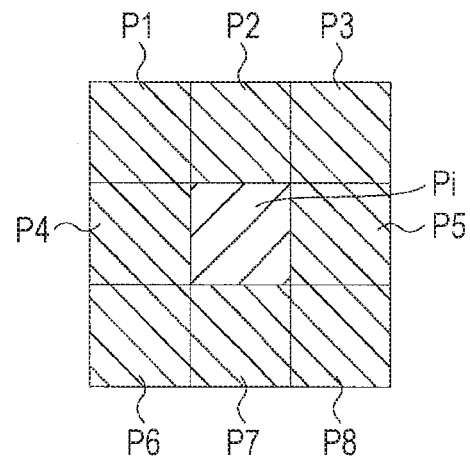
FIGS. 4(a) and 4(b) are views illustrating a focused pixel and adjacent pixels in an image captured by an electronic scope of an electronic endoscope.
Figure 4:
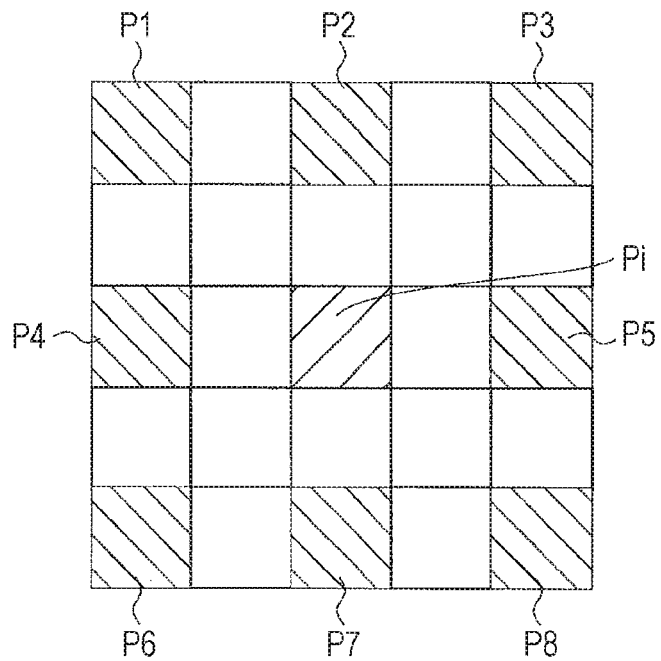

The calculation unit 29 is connected to the system controller 21. The calculation unit 29 is a part that extracts a region that needs to be enhanced in a captured image, stored by imaging a living tissue and called from the image memory 27 via the system controller 21, for example, a concave portion of the living tissue and a region surrounding the concave portion, and performs enhancement processing on this region. FIG. 2 is a block diagram illustrating an example of a configuration of the calculation unit 29. The calculation unit 29 includes a region detection unit 30 and an enhancement processing unit 31. FIG. 3 is a view illustrating an example of imaging of a living tissue by the electronic scope 100. A living tissue A has many concave portions B having different depths in the depth direction when viewed from the electronic scope 100. The electronic scope 100 images the living tissue A including the concave portions B. FIGS. 4(a) and 4(b) are views illustrating a focused pixel and adjacent pixels.

As the living tissue including the plurality of concave portions having different depths is imaged by the electronic scope 100, regions corresponding to the plurality of concave portions having different signal level values are included in the captured image. The region detection unit 30 detects (extracts) a region corresponding to a concave portion.

The region detection unit 30 is configured to detect an enhancement processing target region that is to be enhanced, that is, a region corresponding to a concave portion, from information on pixels of the captured image of the living tissue. The region detection unit 30 sets each pixel of the captured image as a focused pixel (hereinafter, a focused pixel when detecting a region corresponding to a concave portion is referred to as a focused pixel 1), compares signal level values of a plurality of adjacent pixels adjacent to the surrounding of the focused pixel 1 with the focused pixel 1 as the center and a signal level value of the focused pixel 1, and sets the focused pixel 1 as the region corresponding to the concave portion when the signal level value of the focused pixel 1 is lower than a representative value of the signal level values of the plurality of adjacent pixels in at least one pixel array direction among a plurality of pixel array directions of the adjacent pixels arranged around the focused pixel 1. For example, in a case where the representative value is a minimum value of the signal level values of the plurality of adjacent pixels, the focused pixel 1 is set as the region corresponding to the concave portion if the signal level value of the focused pixel 1 is lower than any of the signal level values of the plurality of adjacent pixels. The region detection unit 30 adds a flag to a flag table that holds flag information for each pixel. Note that, as described later, it is determined whether the undulation-enhanced data S in a pixel set as the region of the concave portion has a value larger than a preset value, and a pixel having a value larger than the preset value is set as a final processing target pixel to be enhanced. Thus, the pixel set as the region of the concave portion by the region detection unit 30 is a candidate for a pixel to be subjected to the enhancement processing.

Here, the adjacent pixels are m-th neighboring pixels (m is a natural number) of the focused pixel 1 in the up-down direction, the left-right direction, the upper left-lower right direction, and the upper right-lower left direction. For example, when m is 1, the adjacent pixels are neighboring pixels neighboring the focused pixel 1 in the up-down direction, the left-right direction, the upper left-lower right direction, and the upper right-lower left direction. Here, m is appropriately set. According to the embodiment, it is preferable that the region detection unit 30 extract a concave portion each time while changing m within a predetermined range in consideration of a case where an object has a plurality of various concave portions having different sizes. According to the embodiment, it is preferable to set the range for changing m based on a resolution of a captured image (a distance on the object corresponding to a length of one side of each pixel) or a position of each part of an organ to be imaged.

In the example illustrated in FIG. 4(a), m is 1. In this case, the adjacent pixels are neighboring pixels P1 to P8 neighboring a focused pixel Pi in the up-down direction, the left-right direction, the upper left-lower right direction, and the upper right-lower left direction. Specifically, the adjacent pixels correspond to the pixels P2 and P7 present in the up-down direction with respect to the focused pixel 1, the pixels P4 and P5 present in the left-right direction with respect to the focused pixel 1, the pixels P1 and P8 present in the upper left-lower right direction with respect to the focused pixel 1, and the pixels P3 and P6 present in the upper right-lower left direction with respect to the focused pixel 1.

In the example illustrated in FIG. 4(b), m is 2. In this case, the adjacent pixels correspond to the pixels P2 and P7 which are second neighboring pixels (separated by one pixel) in the up-down direction, the pixels P4 and P5 which are second neighboring pixels (separated by one pixel) in the left-right direction, the pixels P1 and P8 which are second neighboring pixels (separated by one pixel) in the upper left-lower right direction, and the pixels P3 and P6 which are second neighboring pixels (separated by one pixel) in the upper right-lower left direction, with respect to the focused pixel Pi.

The enhancement processing unit 31 is configured to perform enhancement processing on the enhancement processing target region detected by the region detection unit 30. The enhancement processing unit 31 includes a depth data generation unit 31a, an undulation-enhanced data generation unit 31b, and an enhancement processing execution unit 31c.

According to the embodiment, the enhancement processing is performed as follows.

Figure 5:
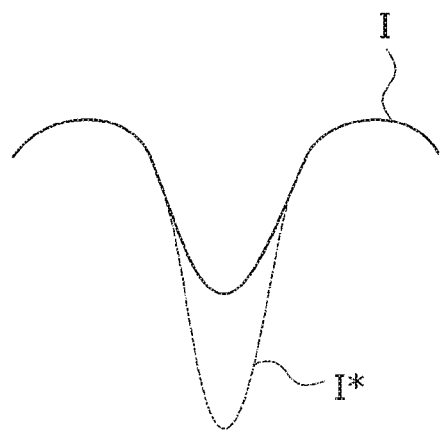
FIG. 5 is a view illustrating an example of enhancement processing performed in one embodiment.

FIG. 5 is a view illustrating an example of the enhancement processing performed in the present embodiment. FIG. 5 illustrates a change of a signal level value in one direction among the pixel array directions by a waveform in order to facilitate understanding.

Figure 6:
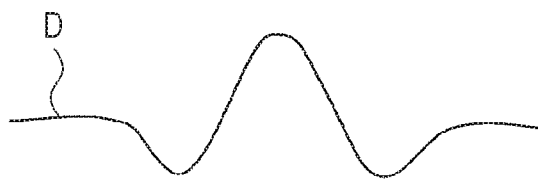
FIGS. 6(a) to 6(c) are views illustrating examples of data used in the enhancement processing of the embodiment.
Figure 6:
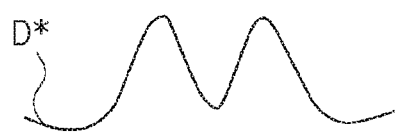
Figure 6:
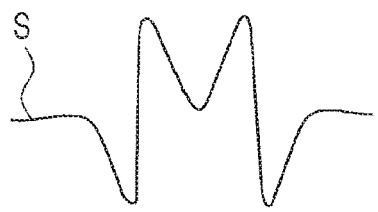

The enhancement processing execution unit 31c generates an enhanced image by adding or subtracting, for example, subtracting the undulation enhancement processing data S to be described later from a waveform I* obtained by enhancing a waveform I of the signal level value $I_{ij}$ illustrated in FIG. 5 based on the depth of the concave portion. The undulation enhancement processing data S is data having information in which a change (inclination) of a signal level value corresponding to a portion where an inclination at a boundary between a concave portion and a convex portions high is made steeper as illustrated in FIG. 6(c) which will be described later. The waveform I* is a waveform corresponding to $I_{ij} - \beta \cdot D_{ij}$ or $I_{ij} - \alpha \cdot I_{ij} - \beta \cdot D_{ij}$ in the formula $I^{**}_{ij} = I_{ij} - \alpha \cdot I_{ij} - \beta \cdot D_{ij} - \gamma \cdot S_{ij}$ which will be described later.

FIGS. 6(a) to 6(c) are views illustrating examples of data used to perform the enhancement processing on the captured image. FIGS. 6(a) to 6(c) illustrate a change of a signal level value in one direction among the pixel array directions by a waveform in order to facilitate understanding.

The depth data generation unit 31a generates the depth data D from the signal level value $I_{ij}$. A data value of the depth data D is calculated based on a difference between the signal level value $I_{ij}$ of the focused pixel 1 of the captured image and a representative value of signal levels of a plurality of adjacent pixels located around the focused pixel 1. For example, the data value of the depth data D is a value obtained by multiplying the difference between the signal level value $I_{ij}$ of the focused pixel 1 and the above-described representative value by a predetermined value. Therefore, the data value of the depth data D includes information on the depth of the concave portion of the living tissue in each pixel.

For example, when signal level values of three pixels (an adjacent pixel, the focused pixel 1, and an adjacent pixel) of the waveform I illustrated in FIG. 5 are 125, 52, and 131, respectively, adjacent pixels in the case of m=1 are used, and a representative value is an average value of signal level values of the adjacent pixels, the representative value is 128 (=(125+131)/2), and a difference (=representative value−signal level value of focused pixel 1) is 76 (=128−52). A value obtained by multiplying this numerical value by the predetermined value is set as the data value of the depth data D of the focused pixel 1.

Here, the adjacent pixels include m-th neighboring pixels (m is a natural number) of the focused pixel 1 in the up-down direction, the left-right direction, the upper left-lower right direction, and the upper right-lower left direction using each pixel of the captured image as the focused pixel 1. For example, when m is 1, the adjacent pixels include neighboring pixels neighboring the focused pixel 1 in the up-down direction, the left-right direction, the upper left-lower right direction, and the upper right-lower left direction. Here, m is appropriately set.

According to the embodiment, the plurality of adjacent pixels used to calculate the difference correspond to the m-th neighboring pixels in at least one direction among four directions of the up-down direction, the left-right direction, the upper left-lower right direction, and the upper right-lower left direction, with the focused pixel 1 as the center.

According to the embodiment, it is preferable that the plurality of adjacent pixels used to calculate the difference be pixels located in any one direction among the up-down direction, the left-right direction, the upper left-lower right direction, and the upper right-lower left direction with respect to the focused pixel 1. For example, the plurality of adjacent pixels may be adjacent pixels in a pixel array direction limited to one direction, two directions, or three directions, or may be adjacent pixels in all the pixel array directions. In addition, the representative value of the signal level values of the adjacent pixels includes a simple average value and a weighted average value of the signal level values of the adjacent pixels. When there are 3 or more adjacent pixels to be compared, the representative value is a simple average value, a weighted average value, a median value, a minimum value, or a maximum value.

FIG. 6(a) illustrates the depth data D generated from the waveform I of the signal level values illustrated in FIG. 5. The depth data generation unit 31a performs such generation of the depth data D for the entire captured image, and acquires the depth data D of the captured image. In the example illustrated in FIG. 6(a), the positive value increases as the depth increases. Therefore, the concave portion illustrated in FIG. 5 has a convex shape in FIG. 6(a).

The undulation-enhanced data generation unit 31b sets each pixel as a focused pixel 2, and generates the undulation-enhanced data S having information in which an inclination at a boundary between a concave portion and a convex portion of surface irregularities of the living tissue is made steep, from the depth data D at a pixel position of the focused pixel 2.

Specifically, the undulation-enhanced data generation unit 31b generates processing data D* as illustrated in FIG. 6(b) from the depth data D. More specifically, the undulation-enhanced data generation unit 31b generates the processing data D* by subtracting an absolute value of a weighted average value of values of the depth data D in peripheral pixels surrounding the focused pixel 2 and a value of the depth data D in the focused pixel 2 from a weighted average value of absolute values of the values of the depth data D in the peripheral pixels surrounding the focused pixel 2 and an absolute value of the value of the depth data D in the focused pixel 2. The peripheral pixels refer to pixels within a predetermined range around the focused pixel 2, for example, all pixels within a range of s pixels×s pixels (s is an odd number of 3 or more and a predetermined value or less). The above s is, for example, 5. The above s is preferably 3 to 9 in that the change (inclination) of the image signal level value at the boundary between the concave portion and the convex portion is adjusted to the steep inclination. The weighted average value is a value obtained by multiplying a value of the depth data D corresponding to each pixel within a predetermined range around the focused pixel 2 by a preset weighting coefficient.

Such a weighted average value functions as a spatial filter, that is, a low-pass filter lpf for the depth data D. Thus, when a process of obtaining a weighted average is expressed as lpf(D) and an absolute value of a positive or negative value is expressed as abs( ), the processing data D* can be expressed as lpf(abs(D))−abs(lpf(D)).

An absolute value abs(D) of the value of the depth data D is a positive value for both regions of a concave portion indicating a positive value and a convex portion indicating a negative value, and changes to reciprocate between a positive value and zero at a portion corresponding to a boundary between the concave portion and the convex portion (portion where a value of the depth data D changes from a positive value to a negative value or from a negative value to a positive value). Thus, in this portion, the weighted average value lpf(abs(D)) (value after the low-pass filter processing) tends to be larger than that in the other portion. On the other hand, regarding the weighted average value lbf(D) of the values of the depth data D, the weighted average value lpf(D) in the portion corresponding to the boundary between the concave portion and the convex portion (portion where a value of the depth data D changes from a positive value to a negative value or from a negative value to a positive value) is smaller than that in the other portion since the positive value and the negative value are subjected to the weighted averaging (cancelled). Therefore, abs(lpf(D)) at the portion corresponding to the boundary between the concave portion and the convex portion is small. Thus, the value of lpf(abs(D))−abs(lpf(D)) in the portion corresponding to the boundary between the concave portion and the convex portion is larger than the value of lpf(abs(D))−abs(lpf(D)) in the other portion. In this manner, it is possible to generate the processing data D* as illustrated in FIG. 6(b) in which the value of the portion corresponding to the boundary between the concave portion and the convex portion becomes large.

Further, the undulation-enhanced data generation unit 31b generates the undulation-enhanced data S as illustrated in FIG. 6(c) by calculating a value obtained by attaching a plus or minus sign to the generated value of lpf(abs(D))−abs(lpf(D)). Here, the concave portion in the depth data D indicates the positive value, and the convex portion indicates the negative value. In this manner, the undulation-enhanced data S having the information with the steep change (inclination) of the signal level value at the boundary between the concave portion and the convex portion of the captured image is generated.

The undulation-enhanced data generation unit 31b determines whether the value of the focused pixel 2 in the undulation-enhanced data S is a value larger than a preset value, sets the focused pixel 2 as a pixel to be subjected to the enhancement processing and assigns a flag to a flag table corresponding to this pixel if the value of the focused pixel 2 is larger than the preset value. As a result, information on the pixel corresponding to the boundary between the concave portion and the convex portion is added to the flag table.

The enhancement processing execution unit 31c generates an enhanced image by adding or subtracting at least a value obtained by multiplying a value obtained by multiplying the value $D_{ij}$ at a position of a corresponding pixel of the depth data D by a constant and a value obtained by multiplying a value $S_{ij}$ at the position of the corresponding pixel of the undulation-enhanced data S by a constant to or from the signal level value $I_{ij}$ of a processing target pixel which is to be enhanced in the captured image. The processing target pixel is a pixel corresponding to a location where a flag is assigned in the flag table, and includes not only the pixel corresponding to the concave portion to which the flag has been assigned by the region detection unit 30 but also the pixel corresponding to the boundary between the concave portion and the convex portion to which the flag has been assigned by the undulation-enhanced data generation unit 31b. Therefore, the enhancement processing of adding or subtracting the value obtained by multiplying the value $D_{ij}$ by the constant and the value obtained by multiplying the value $S_{ij}$ by the constant to or from the signal level value $I_{ij}$ sets, as the processing target, the pixel corresponding to the concave portion to which the flag has been assigned by the region detection unit 30, the pixel corresponding to the boundary between the concave portion and the convex portion to which the flag has been assigned by the undulation-enhanced data generation unit 31b.

According to the embodiment, when a signal level value of the processing target pixel is $I^{}_{ij}$, it is preferable that the enhancement processing execution unit 31c calculate $I^{}_{ij}$ according to the following formula.

$$I^{**}_{ij} = I_{ij} - \alpha \cdot I_{ij} - \beta \cdot D_{ij} - \gamma \cdot S_{ij}$$

Here, α, β, and γ are set constants. Here, a reason why $\alpha \cdot I_{ij}$ is subtracted from $I_{ij}$ is to enhance a region corresponding to a shallow concave portion. A signal level value of a pixel corresponding to the shallow concave portion is higher than a signal level value of a pixel corresponding to the deep concave portion because the concave portion is shallow. Thus, the region corresponding to the shallow concave portion can be enhanced by subtracting $\alpha \cdot I_{ij}$ from $I_{ij}$. However, when the region corresponding to the shallow concave portion is enhanced, a difference in signal level value decreases between the pixel corresponding to the shallow concave portion and the pixel corresponding to the deep concave portion, it becomes difficult to enhance the degree of depth of the concave portion, so that the three-dimensional effect of the surface irregularities of the living tissue, which is the object, is easily lost in the image. However, the enhancement processing execution unit 31c further performs the enhancement processing using $\gamma \cdot S_{ij}$ so that the change of the signal level value at the portion where the inclination at the boundary between the concave portion and the convex portion is steep is made even steeper. Thus, it is possible to suppress the deterioration of the three-dimensional effect of the surface irregularities.

Here, γ is set to zero for the pixel corresponding to the concave portion to which the flag has been assigned by the region detection unit 30 and to which no flag has been assigned by the undulation-enhanced data generation unit 31b, and γ is set to a predetermined value (non-zero value) for the pixel corresponding to the concave portion to which the flag has been assigned by the region detection unit 30 and to which the flag has been assigned by the undulation-enhanced data generation unit 31b.

Figure 7:
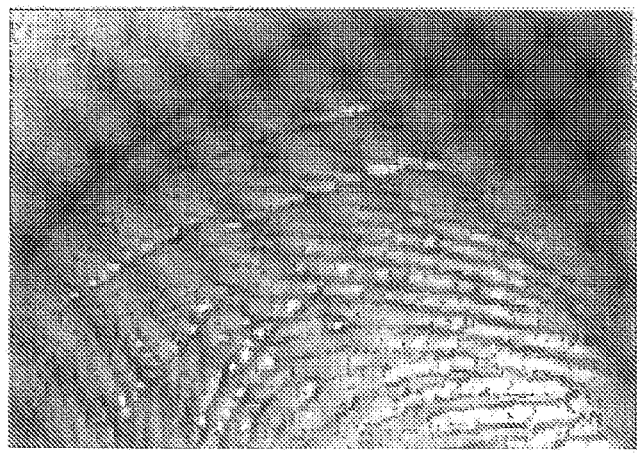
FIG. 7(a) is an image illustrating an example of a conventional enhanced image.
FIG. 7(b) is an image illustrating an example of an enhanced image generated by an enhancement processing execution unit of the embodiment.
Figure 7:
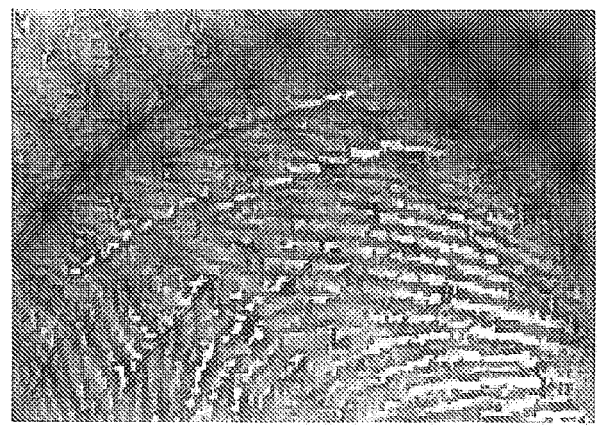

FIG. 7(a) is an image illustrating an example of a conventional enhanced image, and is a result calculated according to $I^{*}_{ij} = I_{ij} - \alpha \cdot I_{ij} - \beta \cdot D_{ij}$. FIG. 7(b) is an image illustrating an example of an enhanced image generated by the enhancement processing execution unit 31c, and is a result calculated according to $I^{**}_{ij} = I_{ij} - \alpha \cdot I_{ij} - \beta \cdot D_{ij} - \gamma \cdot S_{ij}$. In the image illustrated in FIG. 7(b), groove-shaped concave portions are easily recognized. Moreover, a shallow groove-shaped concave portion and a deep groove-shaped concave portion can be easily distinguished and recognized, and a three-dimensional effect is improved as compared with the image illustrated in FIG. 7(a).

Note that, when a captured image is a color image including a plurality of color components such as red, green, and blue, it is preferable that the enhancement processing execution unit 31c generate an enhanced image using a value of the depth data D and a value of the undulation-enhanced data S shared for the signal level values $I_k$ of the color components of the three colors of red, green, and blue according to the embodiment. Since a region of a concave portion is not different depending on the three color components of red, green and blue, but is common. Thus, it is preferable to use the value of the depth data D and the value of the undulation-enhanced data S shared by the color components of the three colors of red, green, and blue.

In addition, it is preferable that the depth data D and the undulation-enhanced data S be data generated using a signal level value of a luminance component of a captured image according to the embodiment. When the captured image is a color image including a plurality of color components such as red, green, and blue, only a signal level value of a certain color component tends to be low even if there is no concave portion due to spectral characteristics of light absorption of a living tissue, and the depth data D and the undulation-enhanced data S using the color components are easily affected by the spectral characteristics of light absorption. Thus, it is preferable to create the depth data D and the undulation-enhanced data S using the signal level value of the luminance component that can relatively reduce the influence of the spectral characteristics of the light absorption of the living tissue.

Figure 8:
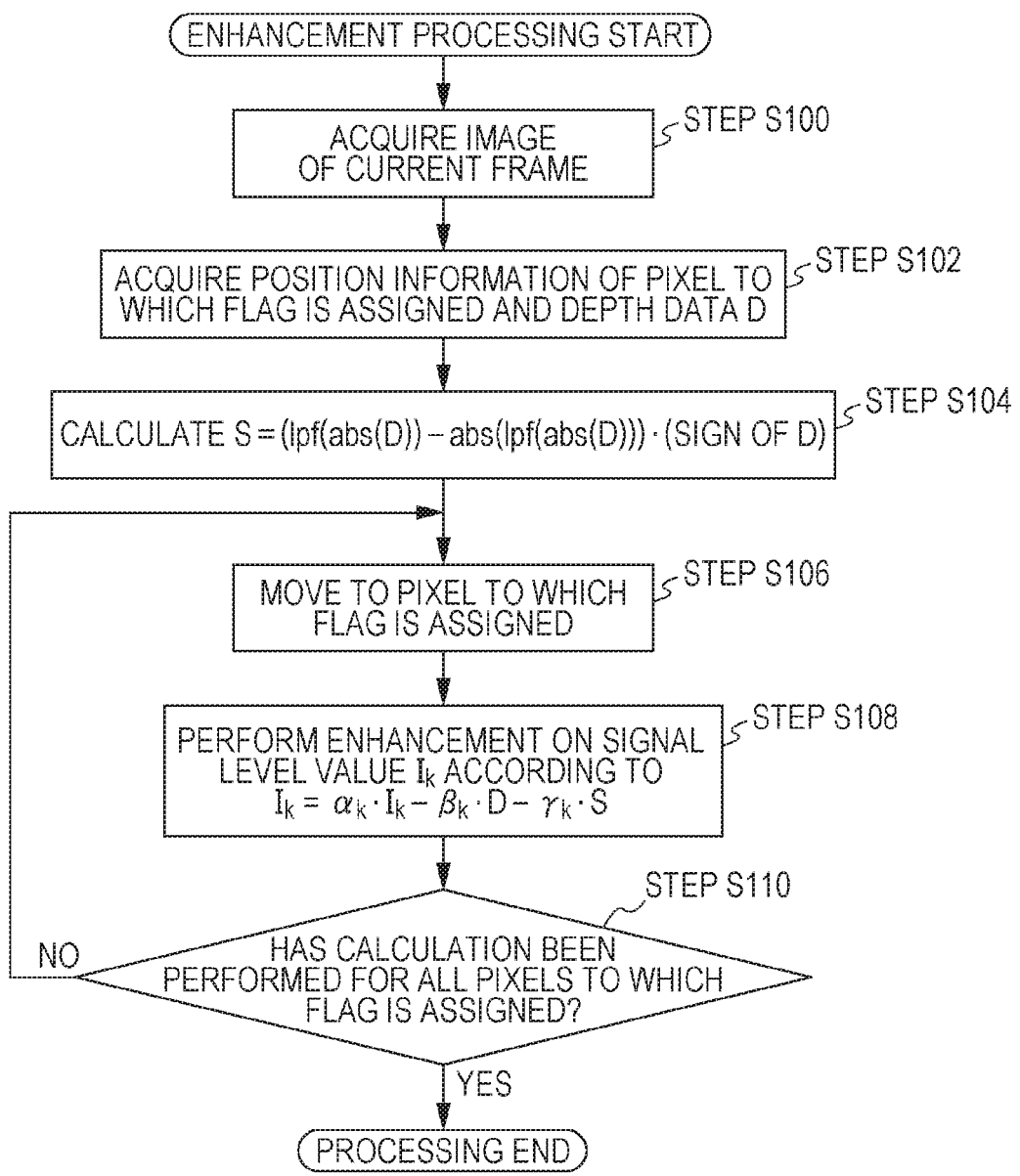
FIG. 8 is a flowchart illustrating an example of a flow of the enhancement processing performed by the enhancement processing unit according to the embodiment.

FIG. 8 is a flowchart illustrating an example of a flow of the enhancement processing performed by the enhancement processing unit 31.

The calculation unit 29 calls a captured image of a current frame captured by the electronic scope 100 and stored in the image memory 27 via the system controller 21 to acquire the captured image (Step S100).

Next, the region detection unit 30 detects a region corresponding to a concave portion in the captured image from the captured image. Thereafter, the depth data generation unit 31a generates and acquires the depth data D as illustrated in FIG. 6(a) for each pixel of the captured image, and further, the undulation-enhanced data generation unit 31b acquires information on a pixel position of a processing target pixel corresponding to a location where a flag has been assigned in a flag table (Step S102).

The undulation enhanced data generation unit 31b calculates S=lpf(abs(D))−abs(lpf(D)) for the captured image (Step S104). At this time, the undulation-enhanced data generation unit 31b sets a pixel having a value larger than a preset value in the undulation-enhanced data S as the processing target pixel, and assigns a flag to a flag table corresponding to the pixel. As a result, the flag is assigned to the position of the flag table corresponding to locations of the concave portion and the boundary between the concave portion and the convex portion. In this manner, the undulation-enhanced data S is generated for each pixel of the captured image.

Next, the enhancement processing execution unit 31c moves to a pixel position (i, j) of the pixel corresponding to the position where the flag has been assigned (Step S106).

The enhancement processing execution unit 31c calculates $I_k-\alpha_k \cdot I_k-\beta_k \cdot D-\gamma_k \cdot S$ for the signal level value II (k is a natural number to identify an R component, a G component, or a B component) of each color component of the RGB color components. Here, in the above formula, i and j indicating the pixel position (i, j) in I, D, and S are not noted, but a natural number variable for identification of the color component is noted. The above-described $\alpha_k$, $\beta_k$, and $\gamma_k$ are constants set for each color component.

The enhancement processing execution unit 31c determines whether or not Steps S106 to S108 have been calculated for all the pixels corresponding to the locations where the flags have been assigned in the flag tables (Step S110).

If the determination is negative (No), the enhancement processing execution unit 31 returns the processing to Step S104, moves to a pixel corresponding to a location where another flag has been assigned, and causes the processing to proceed to Step S106.

Thereafter, if the determination in Step S110 is affirmative (Yes), the enhancement processing is ended. As described above, the enhancement processing is performed on the processing target pixel to which the concave portion flag has been assigned.

According to the embodiment, the enhancement processing execution unit 31c is configured to subtract the value obtained by multiplying the signal level value of the enhancement processing target pixel by the constant α from the signal level of the enhancement processing target pixel, such as $I_k-\alpha_k \cdot I_k$, and thus, can enhance the region corresponding to the shallow concave portion. At this time, the three-dimensional effect of the surface irregularities is easily lost, but the change of the signal level value is adjusted using the undulation-enhanced data S (using $-\gamma_k \cdot S$) such that the steeply inclined portion at the boundary between the concave portion and the convex portion looks even steeper. Thus, it is possible to suppress the deterioration of the three-dimensional effect of the surface irregularities of the living tissue, which is the object, while enhancing the shallow concave region. In this case, a steep inclination at the boundary between the shallow concave portion and the convex portion is relatively gentle as compared to the steep inclination at the boundary between the deep concave portion and the convex portion, and thus, it is easy to identify the shallow concave portion and the deep concave portion depending on the degree of the inclination at the boundary between the concave portion and the convex portion.

Since the calculation is performed according to $I_k-\alpha_k \cdot I_k-\beta_k \cdot D-\gamma_k \cdot S$ in the calculation of the enhancement processing performed by the enhancement processing execution unit 31c in Step S108, the enhancement processing can be performed by setting the constants $\alpha_k$, $\beta_k$, and $\gamma_k$ for each color component. The constants $\alpha_k$, $\beta_k$, and $\gamma_k$ can be made, for example, different from each other. As a result, the concave portion is enhanced including a change in color so that the degree of enhancement of the concave portion is increased. At this time, it is preferable that the depth data D and the undulation-enhanced data S be data generated using the signal level value of the luminance component of the captured image.

According to the embodiment, it is preferable that the constants $\alpha_k$ and $\gamma_k$ of the R component have larger values than the constants $\alpha_k$ and $\gamma_k$ of at least one of the G and B color components. Since the living tissue absorbs light in the wavelength band of the blue component and the green component, it is difficult to distinguish the region of the concave portion from a region darkened by light absorption. Thus, it is preferable in that the region corresponding to the concave portion of the living tissue can be enhanced using the signal level value of the R component so as to be distinguishable from the region that absorbs light.

Although the processor for an electronic endoscope and the electronic endoscope system of the present invention has been described in detail as above, the processor for an electronic endoscope and the electronic endoscope system of the present invention are not limited to the above-described embodiment, and may of course be modified or altered in various ways in a range not deviating from the spirit of the present invention.

REFERENCE SIGNS LIST

1 Electronic endoscope system
11 LCB
12 Light distribution lens
13 Objective lens
14 Solid-state image sensor
15 Driver signal processing circuit
16 Memory
21 System controller
22 Timing controller
24 Operation panel
25 Condenser lens
26 Pre-stage signal processing circuit
27 Image memory
28 Post-stage signal processing circuit
29 Calculation unit
30 Region detection unit
31 Enhancement processing unit
100 Electronic scope
200 Processor
300 Monitor

The invention claimed is:

1. A processor for an electronic endoscope, which acquires a captured image of a living tissue and performs enhancement processing, comprising:
   an enhancement processor configured to perform enhancement processing on the captured image of the living tissue,
   wherein the enhancement processor performs operations including:

generating depth data D of a whole captured image by generating a data value representing information on a depth of a concave portion of the living tissue in a first focused pixel based on a difference between a signal level value of the first focused pixel that is each pixel of the captured image and a representative value of signal level values of a plurality of adjacent pixels located around the first focused pixel;

generating a value of undulation-enhanced data S for each pixel of the captured image, which has information with a steeply inclined change of a signal level value of the captured image at a boundary between a concave portion and a convex portion of surface irregularities of the living tissue, from the depth data D; and generating an enhanced image by adding or subtracting at least a value obtained by multiplying a value of the depth data D in a processing target pixel by a constant, and a value obtained by multiplying the value of the undulation-enhanced data S in the processing target pixel by a constant to or from a signal level value of the processing target pixel on which the enhancement processing of the captured image is performed, wherein the undulation-enhanced data S is generated by calculating a value obtained by attaching a plus or minus sign of the depth data D in a second focused pixel to a result obtained by subtracting an absolute value of a weighted average value of values of the depth data D of peripheral pixels surrounding the second focused pixel and a value of the depth data D of the second focused pixel from a weighted average value of an absolute value of the value of the depth data D in the second focused pixel and absolute values of the values of the depth data D of the peripheral pixels surrounding the second focused pixel that is each pixel of the captured image.

2. The processor for an electronic endoscope according to claim 1, wherein
the peripheral pixels are all pixels excluding the second focused pixel in a range of s pixels×s pixels (s is an odd number of 3 or more) around the second focused pixel.

3. The processor for an electronic endoscope according to claim 2, wherein
s is an odd number in a range of 3 to 9.

4. The processor for an electronic endoscope according to claim 1, wherein
a pixel having a value larger than a preset value in the undulation-enhanced data S is set as the processing target pixel.

5. The processor for an electronic endoscope according to claim 1, wherein
the adjacent pixels are m-th neighboring pixels (m is a natural number of one or more) in at least one pixel array direction among four directions of an up-down direction, a left-right direction, an upper left-lower right direction, and an upper right-lower left direction with the first focused pixel as a center.

6. The processor for an electronic endoscope according to claim 5, wherein
the first focused pixel is set as a candidate for the processing target pixel when the signal level value of the first focused pixel is lower than the representative value of the signal level values of the m-th neighboring pixels.

7. The processor for an electronic endoscope according to claim 1, wherein
the representative value is a simple average value, a weighted average value, a median value, a minimum value, or a maximum value of the signal level values of the adjacent pixels.

8. The processor for an electronic endoscope according to claim 1, wherein
the enhanced image is generated by subtracting a value obtained by multiplying the signal level value of the processing target pixel by a constant from the signal level value of the processing target pixel as well as adding or subtracting the value obtained by multiplying the value of the depth data D by the constant and the value obtained by multiplying the value of the undulation-enhanced data S by the constant to or from the signal level value of the processing target pixel.

9. The processor for an electronic endoscope according to claim 1, wherein
the signal level values of the captured image include signal level values $I_k$ of color components of three colors of red, green, and blue, where k is a variable to identify red, green, or blue color component and is a natural number, and
the enhanced image is generated using the value of the depth data D and the value of the undulation-enhanced data S shared by the signal level values $I_k$ of the color components of the three colors of red, green, and blue.

10. The processor for an electronic endoscope according to claim 9, wherein
the depth data D and the undulation-enhanced data S are data generated using a signal level value of a luminance component of the captured image,
in the generating the enhanced image, a signal level value $I_k^*$ of the enhanced image is generated according to
$I_k^* = I_k - \alpha_k \cdot I_k - \beta_k \cdot D - \gamma_k \cdot S$, and
$\alpha_k$, $\beta_k$, and $\gamma_k$ are constants and have different values among the color components of the three colors.

11. The processor for an electronic endoscope according to claim 10, wherein $\alpha_k$ and $\gamma_k$ of the red color component have larger values than $\alpha_k$ and $\gamma_k$ of at least one of the green and blue color components.

12. An electronic endoscope system comprising:
the processor for an electronic endoscope according to claim 1; and
an electronic endoscope which is connected to the processor for an electronic endoscope and outputs the captured image of the living tissue.

* * * * *